US007127096B2

(12) United States Patent
Kaufman et al.

(10) Patent No.: US 7,127,096 B2
(45) Date of Patent: Oct. 24, 2006

(54) METHOD AND SOFTWARE FOR IMPROVING CORONARY CALCIUM SCORING CONSISTENCY

(75) Inventors: Leon Kaufman, San Francisco, CA (US); Joseph W. Carlson, Kensington, CA (US)

(73) Assignee: Accuimage Diagnostics Corp., So. San Francisco ( * ) Notice: Subject to any disclaimer, the term of this patent is extended or adjusted under 35 U.S.C. 154(b) by 523 days.

(21) Appl. No.: 10/126,463

(22) Filed: Apr. 18, 2002

(65) Prior Publication Data

US 2003/0095693 A1    May 22, 2003

Related U.S. Application Data

(60) Provisional application No. 60/332,452, filed on Nov. 20, 2001.

(51) Int. Cl.
G06K 9/00 (2006.01)
G06K 9/40 (2006.01)
G06K 9/36 (2006.01)
G06K 9/32 (2006.01)
G01D 18/00 (2006.01)

(52) U.S. Cl. .................. 382/131; 382/263; 382/264; 382/280; 382/299; 378/207

(58) Field of Classification Search ........ 382/128–132, 382/263, 264, 279, 280, 299; 378/207; 702/85
See application file for complete search history.

(56) References Cited

U.S. PATENT DOCUMENTS

| 4,135,247 | A | * | 1/1979 | Gordon et al. ............... 378/11 |
| 4,613,754 | A | * | 9/1986 | Vinegar et al. ........ 250/252.1 |
| 4,974,598 | A | | 12/1990 | John |
| 5,170,439 | A | * | 12/1992 | Zeng et al. ................. 382/131 |
| 5,325,293 | A | | 6/1994 | Dorne |
| 5,335,260 | A | | 8/1994 | Arnold |
| 5,396,886 | A | | 3/1995 | Cuypers |
| 5,446,799 | A | * | 8/1995 | Tuy ........................... 382/132 |
| 5,528,492 | A | | 6/1996 | Fukushima |
| 5,549,117 | A | | 8/1996 | Tacklind et al. |
| 5,570,404 | A | | 10/1996 | Liang et al. |
| 5,581,460 | A | | 12/1996 | Kotake et al. |
| 5,704,371 | A | | 1/1998 | Shepard |
| 5,729,620 | A | | 3/1998 | Wang |
| 5,768,406 | A | | 6/1998 | Abdel-Motialeb |
| 5,807,256 | A | | 9/1998 | Taguchi et al. |
| 5,832,450 | A | | 11/1998 | Myers et al. |
| 5,832,504 | A | | 11/1998 | Tripathi et al. |
| 5,895,461 | A | | 4/1999 | De La Huerga et al. |
| 5,911,133 | A | | 6/1999 | Soble |

(Continued)

OTHER PUBLICATIONS

Agatston et al., "Quantification of Coronary Artery Calcium Using Ultrafast Computed Tomography," *JACC,* (Mar. 15, 1990) vol. 15, No. 4, pp. 827-832.

(Continued)

*Primary Examiner*—Bhavesh M. Mehta
*Assistant Examiner*—Anthony Mackowey
(74) *Attorney, Agent, or Firm*—Townsend and Townsend and Crew LLP

(57) ABSTRACT

Methods and devices for improving the machine-to-machine and temporal (e.g., inter and intra-machine) and database consistency of coronary calcium scoring by applying a filtering algorithm that sharpens and/or smoothes the image so as to return a filtered image having a spatial resolution of a certain reference value.

66 Claims, 9 Drawing Sheets

U.S. PATENT DOCUMENTS

| | | | |
|---|---|---|---|
| 5,950,207 | A | 9/1999 | Mortimore et al. |
| 5,986,662 | A | 11/1999 | Argiro et al. |
| 6,029,138 | A | 2/2000 | Khorasani et al. |
| 6,049,622 | A | 4/2000 | Robb et al. |
| 6,058,322 | A | 5/2000 | Nishikawa et al. |
| 6,061,419 | A * | 5/2000 | Hsieh et al. .................... 378/4 |
| 6,061,695 | A | 5/2000 | Slivka et al. |
| 6,083,162 | A | 7/2000 | Vining |
| 6,088,488 | A * | 7/2000 | Hardy et al. ................ 382/278 |
| 6,110,109 | A | 8/2000 | Hu et al. |
| 6,122,351 | A | 9/2000 | Schlueter, Jr. et al. |
| 6,133,918 | A | 10/2000 | Conrad et al. |
| 6,137,898 | A | 10/2000 | Broussard et al. |
| 6,190,334 | B1 | 2/2001 | Lasky et al. |
| 6,205,871 | B1 | 3/2001 | Saloner et al. |
| 6,226,352 | B1 | 5/2001 | Salb |
| 6,233,304 | B1 * | 5/2001 | Hu et al. ....................... 378/8 |
| 6,253,214 | B1 | 6/2001 | Hall et al. |
| 6,304,848 | B1 | 10/2001 | Singer |
| 6,317,617 | B1 | 11/2001 | Gilhujis et al. |
| 6,320,931 | B1 | 11/2001 | Arnold |
| 6,348,793 | B1 | 2/2002 | Balloni et al. |
| 6,366,638 | B1 * | 4/2002 | Hsieh et al. .................. 378/19 |
| 6,430,430 | B1 | 8/2002 | Gosche |
| 6,460,003 | B1 * | 10/2002 | Kump et al. .................. 702/85 |
| 6,674,834 | B1 * | 1/2004 | Acharya et al. .............. 378/18 |
| 6,674,880 | B1 * | 1/2004 | Stork et al. ................. 382/128 |
| 6,697,451 | B1 * | 2/2004 | Acharya et al. .............. 378/18 |
| 6,813,393 | B1 * | 11/2004 | Takeo ......................... 382/299 |
| 6,928,182 | B1 * | 8/2005 | Chui .......................... 382/131 |
| 2001/0031076 | A1 | 10/2001 | Campanini et al. |
| 2002/0081006 | A1 | 6/2002 | Rogers et al. |
| 2002/0193687 | A1 | 12/2002 | Vining et al. |
| 2003/0048867 | A1 * | 3/2003 | Acharya et al. .............. 378/18 |
| 2003/0095695 | A1 | 5/2003 | Arnold |
| 2003/0165262 | A1 | 9/2003 | Nishikawa et al. |
| 2003/0176780 | A1 | 9/2003 | Arnold et al. |
| 2003/0215124 | A1 | 11/2003 | Li |
| 2004/0069951 | A1 * | 4/2004 | Jones et al. ................. 250/369 |
| 2005/0281478 | A1 | 12/2005 | Kaufman et al. |

OTHER PUBLICATIONS

Brown et al., "Method for Segmenting Chest CT Image Data Using an Anatomical Model: Preliminary Results," *IEEE Transactions on Medical Imaging*, (Dec. 1997) vol. 16, No. 6, pp. 828-839.

Grundy, Scott M., MD, Ph.D., "Coronary Plaque as a Replacement for Age as a Risk Factor in Global Risk Assessment," *The American Journal of Cardiology*, (Jul. 19, 2001) vol. 88 (2A), pp. 8E-11E.

Hoff et al., "Age and Gender Distributions of Coronary Artery Calcium Detected by Electron Beam Tomography in 35,246 Adults," *The American Journal of Cardiology*, (Jun. 15, 2001) vol. 87, pp. 1335-1339.

Rumberger et al., "Electron Beam Computed Tomographic Calcium Scanning: A Review and Guidelines for Use in Asymptomatic Persons," *Mayo Foundation for Medical Education and Research*, (Mar. 1999) vol. 74, pp. 243-252.

Schmermund et al., "An Algorithm for Noninvasive Identification of Anglographic Three-Vessel and/or Left Main Coronary Artery Disease in Symptomatic Patients on the Basis of Cardiac Risk and Electron-Beam Computed Tomographic Calcium Scores," *Journal of the American College of Cardiology*, (1999) vol. 33, No. 2, pp. 444-452.

Sutton-Tyrell et al., "Usefulness of Electron Beam Tomography to Detect Progression of Coronary and Aortic Calcium in Middle-Aged Women," *The American Journal of Cardiology*, (Mar. 1, 2001) vol. 87, pp. 560-564.

Zhu et al., "Accuracy of Area Measurements Made From MR Images Compared With Computed Tomography," *Journal of Computer Assisted Tomography* (Jan./Feb. 1986) vol. 10, No. 1, pp. 96-102.

U.S. Appl. No. 10/844,026, filed May 12, 2004, Kaufman.
U.S. Appl. No. 10/234,984, filed Sep. 3, 2003, Kaufman.
U.S. Appl. No. 10/096,356, filed Mar. 11, 2002, Rumberger.

Acharya, K.C. et al., "Calcium score with electron beam and single slice helical CT: A three center study," Radiological Society of North America 86th Annual Meeting Abstract Book Suppl, 142:232-233 (2000).

Achenbach, S. et al., "Overlapping cross-sections significantly improve the reporducibility of coronary calcium measurements by electron beam tomography: A phantom study" *J. Comput. Assist. Tomogr.*, 25(4):569-573 (2001).

"ADC Full Leg/Full Spine Software" Product Brochure by AGFA-Gevaert N.V. Belgium, B-2640 Mortsel-Belguim NE3JT GB 00200101, 2 pages total.

Agatston, A.S. et al., "Electron beam CT coronary calcium predicts future coronary events (abstr)," Abstract 2097, *Circulation*, 94:1/360 (1996).

Arad, Y. et al., "Predictive value of electron beam computed tomography of the coronary arteries: 19-month follow-up of 1173 asymptomatic subjects," *Circulation*, 93:1951-1953 (1996), printed from internet Aug. 17, 2004.

Baumgart, D. et al., "Comparison of electron beam computed tomography with intracoronary ultrasound and coronary angiography for detection of coronary atheroselerosis," *JACC*, 30(1):57-64 (1997).

Becker, C.R. et al., "Helical and single-slice conventional CT versus electron beam CT for the quantification of coronary artery calcification," *A.J.R.*, 174:543-547 (2000).

Bielak, L.F. et al., "Coronary artery calcification measured at electron-beam CT: Agreement in dual scan runs and change over time," *Radiology*, 218(1):224-229(2001).

Boese, J.M. et al., "Optimizing temporal resolution in CT with retrospective ECG gating," *Radiologe*, 40(2):123-129 (2000). [in German].

Callister, T.Q. et al., "Coronary artery disease: Improved reproducibility of calcium scoring with an electron-beam CT volumetric method," *Radiology*, 208:807-814 (1998).

Carr, J.J. et al., "Evaluation of subsecond gated helical CT for quantification of coronary artery calcium and comparison with electron beam CT," *A.J.R.*, 174:915:921 (2000).

Detrano, R. (Hong) et al., "Prognostic value of coronary calcification and angiographic stenoses in patients undergoing coronary angiography," *JACC*, 27:285-290 (1996).

Georgiou, D. et al., "Screening patients with chest pain in the emergency department using electron beam tomography: A follow-up study," *JACC*, 38(1):105-110 (2001).

Goldin, J.G. et al., "Spiral versus electron-beam CT for coronary artery calcium scoring," *Radiology*, 221:213-221 (2001).

Hoffman, U. et al., "Precision and variability of multiple scoring methods for ex vivo quantification of vascular calcification by multidetector computed tomography," Abstract 30, *Radiology*, 225(P):240 (2002).

Hong, C. et al., "Coronary artery calcium: absolute quantificaton in nonenhanced and contrast-enhanced multi-detector row CT studies," *Radiology*, 223:474-480 (2002).

Hong, C. et al., "Coronary artery calcium: accuracy and reproducibility of measurements with multi-detector row CT—assessment of effects of different thresholds and quantification methods," *Radiology*, 227:795-801 (2003).

Kaufman et al., "Quantitative Characterization of Signal-to-Noise Ratios in Diagnostic Imaging Instrumentation," *Prog. Nucl. Med.*, 7:1-17 (1981).

Kaufman et al., "Methods for Evaluation of Diagnostic Imaging Instrumentation," *Phys. Med. Biol.*, 26(1):101-112 (1981).

Kaufman et al., "Generalized Methodology for the Comparison of diagnostic Imaging Instrumentation," AFIPS Press, 49:445-451 (1980).

Kaufman et al., "Measurement of the Texture Contribution to Image Noise in Scintigrams," Applications of Optical Instrumentation in Medicine VII, SPIE 233:134-136 (1980).

Lawler, L.P. et al., "Coronary artery calcification scoring by multidetector CT: Is it reliable and reproducible?" Radiological

*Society of North America 86th Annual Meeting Abstract Book Suppl.,* p. 502, abstract # 1127 (2000).

Mao, S. et al., "Effect of electrocardiogram triggering on reproducibility of coronary artery calcium scoring," *Radiology,* 220:707-711 (2001).

Mao, S. et al., "Improved reproducibility of coronary artery calcium scoring by electron beam tomography with a new electrocardiographic trigger method," *Invest. Radiol.,* 26(7):363-367 (2001).

Möhlenkamp, S. et al., "Reproducibility of two coronary calcium quantification algorithms in patients with different degrees of calcification," *Int. J. Cardiovasc. Imaging,* 17:133-142 (2001).

Ohnesorge, B.M et al., "Cardiac imaging by means of electrocardiographically gated multisection spiral CT: Initial Experience," *Radiology,* 217:564-571 (2000).

Ohnesorge, B.M. et al., "Reproducibility of coronary calcium scoring with EBCT and ECG-gated multi-slice spiral CT," *Radiological Society of North America 86th Annual Meeting Abstract Book* abstract 143, p. 233, (2000).

Qanadli, S.D. et al., "Volumetric quantification of coronary artery calcifications using dual-slice spiral CT scanner: Improved reproductibility of measurements with 180° linear interpolation algorithm," *J. Comput. Assist. Tomogr.,* 25(2):278-286 (2001).

Raggi, P. et al., "Use of electron beam tomography data to develop models for prediction of hard coronary events," *American Heart J.,* 141(3):375-382 (2001).

Raggi et al., "Calcium Scoring of the Coronary Artery by Electron Beam CT: How to Apply an Individual Attenuation Threshold" (Feb. 2002) AJR vol. 178, pp. 497-502.

Rumberger et al., "A rosetta stone for coronary calcium risk stratification: Agatston, volume and mass scores in 11,490 individuals," *AJR,* 181:743-748 (2003).

Secci, A. et al., "Electron Beam computed tomographic coronary calcium as a predictor of coronary events: Comparison of two protocols," *Circulation,* 96:1122-1129 (1997), printed from internet Aug. 17, 2004.

Stanford, W. et al., "Coronary artery calcium: Comparison of electron beam CT with helical CT," *Radiological Society of North America 86th Annual Meeting Abstract Book,* abstract 1586, p. 589 (2000).

Takahashi, N. et al., "Coronary calcium scoring using multi-slice CT: Evaluation of interscan variability and optimal scan tub current," *Radiological Society of North America 86th Annual Meeting Abstract Book,* abstract 1126, p. 501 (2000).

Wexler, L. et al., "Coronary artery calcification: pathophysiology, epidemiology, image methods and clinical implications: A scientific statement for health professionals from the American Heart Association," Circulation 94:1175-1192 (1996), printed form internet Aug. 17, 2004.

Wilson et al., "Prediction of coronary heart disease using risk factor categories," *Circulation,* 97:1837-1847 (1998).

* cited by examiner

METHOD AND SOFTWARE FOR IMPROVING CORONARY CALCIUM SCORING CONSISTENCY

CROSS-REFERENCE TO RELATED APPLICATIONS

The present application claims benefit under 37 C.F.R. § 1.78 to Provisional Patent Application Ser. No. 60/332,452, filed Nov. 20, 2001, the complete disclosure of which is incorporated herein by reference.

The present application is also related to U.S. patent application Ser. No. 09/860,030, filed May 16, 2001, entitled "Accreditation Maintenance Through Remote Site Monitoring," Ser. No. 09/908,466, filed Aug. 17, 2001, entitled "Methods for Generating a Lung Report," and Ser. No. 10/096,356, filed Mar. 11, 2002, entitled "Systems, Methods, and Software for Generating a Risk Report," the complete disclosures of which are incorporated herein by reference.

BACKGROUND OF THE INVENTION

The present invention generally relates to medical imaging software, methods, and databases. Specifically, the present invention relates to improving machine-to-machine and temporal (e.g., inter and intra-machine) consistency of coronary calcium scoring by using an algorithm that can either sharpen or smooth the image, so as to return the spatial resolution of the processed image to a certain reference value.

Coronary artery calcium quantitation is a major focus in the effort to assess risk for coronary heart disease, to monitor progression of plaque development, and to potentially assess therapies and interventions designed to reduce mortality from coronary heart disease. (See Rumberger J. A. et al, "Electron Beam Computed Tomographic Coronary Calcium Scanning: A Review and Guidelines for Use in Asymptomatic Persons," Mayo Clinic Proc. 1999; 74:243–252 and Schmermund A., et al, "An Algorithm for Noninvasive Identification of Angiographic Three-Vessel and/or left Main Coronary Artery Disease in Symptomatic Patients," J. Am. Coll. Cardiology 1999; 33:444–452, the complete disclosure of which are incorporated herein by reference). Although the current orthodoxy is that the rupture of soft plaque and subsequent thrombus formation is the major precursor of acute coronary events, in most individuals it is believed that coronary calcium burden is also a valid surrogate or indicator of total plaque burden, including soft plaque.

The assessment of risk from coronary calcium is generally a two-step process: First, calcium burden is quantitated by a "scoring" algorithm, most commonly with the Agatston scale. (See Agatston A. S. et al, "Quantification of Coronary Artery Calcium Using Ultrafast Computed Tomography," J. Am. Coll. Cardiology 1990; 15:827–832, the complete disclosure of which is incorporated herein by reference). Second, the measured calcium burden, age, and gender of the individual are used to rank the individual against his or her age-matched cohort.

X-rays in the energy range used for radiography are highly sensitive to the presence of vascular and extra-vascular calcium in the coronary arteries. Computed tomography (CT), with its ability to provide thin sections and three-dimensional slice registration, increases the sensitivity to the presence of small amounts of calcium in the patient's vasculature. Interestingly enough, the voxel volume of CT and digital radiography are not dramatically different. Compared to CT, radiography has much better in-plane resolution but much poorer resolution along the beam. The complexity of structures seen in a plane projection, however, makes the task of quantitating coronary calcium in a radiograph difficult.

Today, thousands of CT scanners perform coronary calcium scoring measurements and thereafter refer the measurements to a database. For example, a database of over 35,000 subjects has been accumulated by the University of Illinois at Chicago. See Hoff J. A. et al., "Age and Gender Distributions of Coronary Artery Calcium Detected by Electron Beam Tomography in 35,246 Adults," Am. J. Cardiology 2001; 87:1335–1339, the complete disclosure of which is incorporated herein by reference. Calcium scores (e.g., Agatston Score or volume score) from an individual subject are compared to this database on the basis of age and gender of the patient. Most of the subjects in the existing database are Caucasian and middle to high socio-economic status, as well as asymptomatic, more males than females, and in the age range of 40–70 years of age. Because of the inherent differences in individual CT scanners and operators, there is considerable controversy as to whether calcium scores from different CT units can be compared to the established databases.

The controversy generally focuses on technology issues (e.g., the differences between helical CT scanners and electron beam CT scanners). Much attention was paid to time resolution and scanner calibration. Scanner calibration assures the HU scale and is well handled by the calibration procedures implemented by manufacturers. Blurring and motion artifacts due to heart motion can either increase or decrease the calcium score, depending on the particulars of the lesion and its motion.

Such a controversy, however, fails to account for operational parameters, machine maintenance, population variability, and spatial resolution. For lesions that have a dimension even a few times larger than the full-width-half-maximum (FWHM) of the scanner point spread function (PSF), both peak intensity and the apparent area of the lesion will be affected by the imaging device's spatial resolution. The spatial resolution of a scanner will depend on its x-ray source and detector configuration, as well as on reconstruction kernels and filters. In addition, the spatial resolution will change as the x-ray source ages.

Unfortunately, there is no process today to monitor and correct for temporal differences or changes in CT scanners, differences in scanner operating settings, or design factors, which vary among manufacturers and operators. Therefore, both the usefulness and quality of the databases, and the relationship of a particular individual to the population in the database may be degraded by uncertainties in the spatial resolution with which the database and the individual subject images were acquired.

Consequently, what is needed are methods and software that can improve the coronary calcium scoring consistency between a plurality of imaging machines or during the lifetime of a machine.

BRIEF SUMMARY OF THE INVENTION

The present invention provides methods, software, devices, databases, and systems for improving the calcium scoring consistency between imaging machines.

The present invention can periodically monitor a spatial resolution (FWHM) of an imaging device, such as a CT scanner. The spatial resolution can be measured once a day, once a week, twice a week, once a month, twice a month, or the like. The measured spatial resolution can be compared to a reference spatial resolution so that a filter or correction algorithm can be generated so as to substantially match the spatial resolution of the scanner to the reference spatial resolution.

Spatial resolution affects, in a predictable manner, calcium scores for lesions that are even a few times larger than the spatial resolution of the scanner, which is typically 0.9 mm FWHM to 1.7 mm FWHM. Because there is no one-to-one correspondence between the effects of changing spatial resolution and the Agatston scoring process, the Agatston Score itself cannot be corrected once measured. The present invention provides methods which standardize CT images to a reference spatial resolution before calcium scoring, so that the calcium scoring results will be independent of the scanner's spatial resolution.

Since all of the scores that are stored in a database will have been filtered to a substantially uniform spatial resolution (preferably to a reference resolution that is within a narrow range, e.g., 5–7%), the spatial resolution of the image will have a reduced effect on the coronary calcium scores and a more accurate comparison between calcium scores of different people or of the same person at different times in their lifetime can be performed.

Advantageously, the methodology of the present invention reduces the effect of temporal and inter-scanner performance differences, and allows for the development of a larger scale database which can use information from many different scanners. In one aspect, the present invention provides a measurement method that accurately reflects the volume of the lesion as presented. The methodology of the present invention opens the way to monitoring of temporal and inter-scanner performance. The methodology can also operate scanners so that these temporal differences are reduced, and preferably eliminated.

One exemplary method comprises imaging a phantom with an imaging device. A spatial resolution of the image (typically referred herein as FWHM) of the phantom is measured and the measured spatial resolution of the phantom is compared against a reference spatial resolution FWHM(ref) as set by the operator. The reference FWHM(ref) may be an arbitrary value to which various centers agree by consensus, it may be the FWHM at the start of operation of a CT scanner, it may be the FWHM with which the reference database was acquired, or any other appropriate value. A filter algorithm is chosen that can be used to alter the spatial resolution of the image of the phantom and thus confirm that the correction produces images that substantially match the reference spatial resolution. The filter algorithm is applied to images thereafter acquired with the imaging device to create a filtered image that has a spatial resolution that substantially matches the reference spatial resolution.

In exemplary embodiments, the phantom of the present invention comprises a collection of objects of known characteristics. In one preferred embodiment, the phantom includes a plurality of aluminum wires running through a slice direction.

Depending on the spatial resolution of the images, the filter algorithm may smooth or sharpen the image data so that the measured spatial resolution FWHM becomes equal to the reference FWHM(ref). There are various ways by which this can be accomplished. For example, in a reconstruction, the data from CT detectors can be filtered before the back-projection that yields an image. This filtering can be adjusted by multiplying the signal distribution along the detectors by set of weights designed to yield the desired spatial resolution.

After the image is reconstructed, the reconstructed image can be convolved with one of the many filters known in the state-of-the-art (Gaussian, Fourier, Cubic, etc.) so that the resolution is adjusted to the desired value; or, the image can be inverse Fourier Transformed, the two-dimensional distribution multiplied by set of weights designed to yield the desired result (i.e., filtered), and the result Fourier Transformed to obtain an image with the desired FWHM.

It should be appreciated that it may be possible to assess the spatial resolution of the scanner without having to use a phantom to obtain it. In such cases, the present invention can compare the spatial resolution of the imaging scanner against a reference spatial resolution (without using a phantom). A filter algorithm can be chosen that will alter the spatial resolution of the image of the phantom to substantially match the reference spatial resolution. The filter algorithm can be applied to the images thereafter acquired with the imaging device to create a filtered image that has a spatial resolution that substantially matches the reference spatial resolution.

In a further aspect, the present invention provides a method of improving a comparison of images. The method comprises providing an algorithm and obtaining image(s) with an imaging device. The algorithm can be applied to the obtained image(s) to adjust a spatial resolution of the obtained image(s) to create resolution-adjusted image(s) that have a spatial resolution that substantially matches a reference spatial resolution.

In yet another aspect, the present invention provides a system for improving coronary calcium scoring consistency. The system includes an imaging unit that measures a spatial resolution (typically through use of a phantom). A computer system can be coupled to the imaging unit and will include a memory that stores a reference spatial resolution. The computer system will also have means for comparing the measured spatial resolution with the reference spatial resolution stored in the memory and means for creating a resolution-adjusted images in which the spatial resolution of the resolution-adjusted images are adjusted to match the reference spatial resolution.

In another aspect, the present invention provides a phantom for calibrating a spatial resolution of an imaging device. The phantom comprises a housing and a plurality of substantially cylindrical bodies positioned in a spaced configuration within the housing.

Each of the cylindrical bodies will typically have a diameter that is between approximately 0.1 times the full width half maximum and 3.0 times the full width half maximum of the imaging device.

In exemplary embodiments, the cylindrical bodies are aluminum or hydroxy apatite wires that are embedded in a low density matrix, such as plastic and/or water. In one preferred embodiment, the longitudinal axes of the plurality of aluminum wires run through a slice direction.

In another aspect, the present invention provides a method of improving the comparison of images. The method comprises obtaining at least one image with an imaging device. An algorithm is applied to the obtained image(s) to adjust a spatial resolution of the obtained image(s) to create resolution-adjusted image(s) that have a spatial resolution that substantially matches a reference spatial resolution.

In yet another aspect, the present invention provides a database for storing coronary calcium information. The database comprises calcium scores from a plurality of filtered images comprising a spatial resolution that has been filtered to substantially match a reference spatial resolution.

In a further aspect, the present invention provides a method of monitoring the performance of an imaging device. The spatial resolution of the imaging device can be periodically measured. A log of the measured spatial resolution can be maintained such that if the spatial resolution is not within a predetermined range of the previous measurements or a reference spatial resolution, a message can be delivered to personnel of the imaging facility or the manufacturer of the imaging device informing them that the imaging device needs maintenance, or the personnel may inspect the database to ascertain whether this is the case.

For a further understanding of the nature and advantages of the present invention, reference should be made to the following detailed description in conjunction with the accompanying drawings.

DETAILED DESCRIPTION OF THE INVENTION

Figure 1:
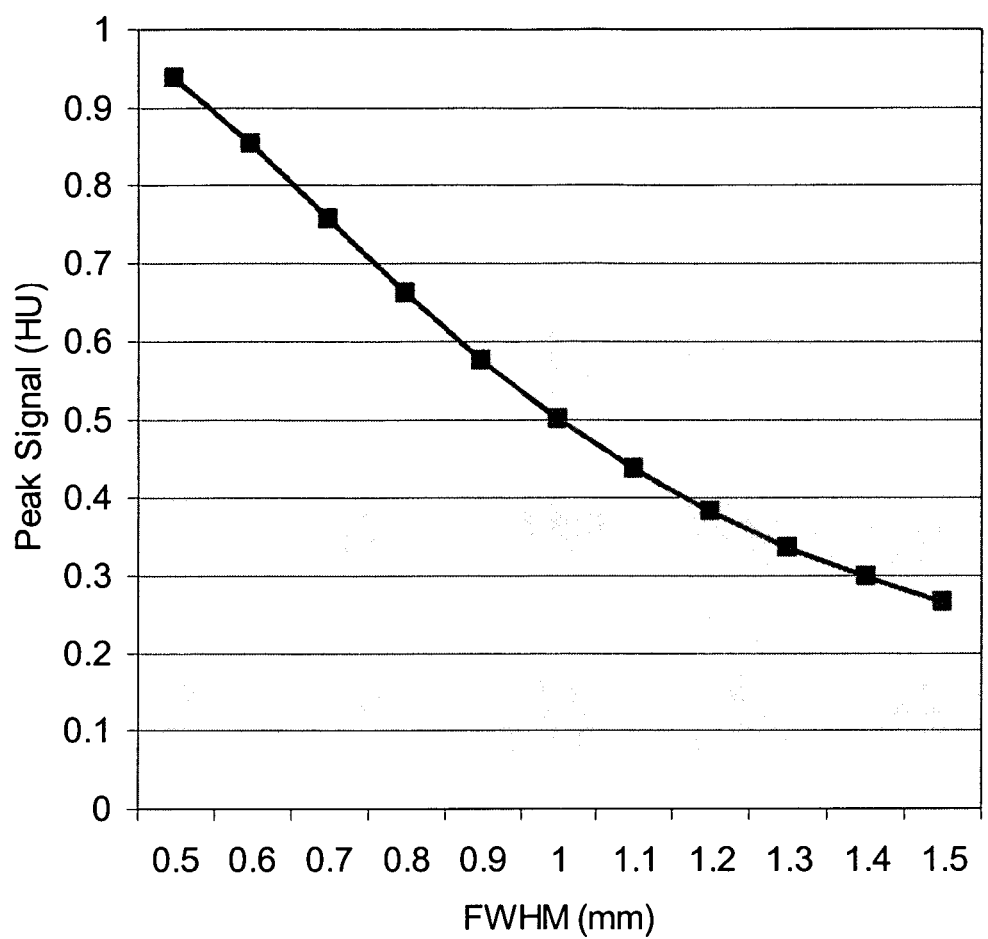
FIG. 1 illustrates a peak signal for a 1 mm-diameter cylindrical lesion spanning a whole slice as a function of CT scanner resolution.

The present invention provides methods, systems, and software for monitoring the spatial resolution of an imaging device so as to improve the consistency of calcium scoring. A filtering algorithm can be used to sharpen or smooth the images obtained by the imaging device so as to alter the spatial resolution of the image to that of a predetermined reference value so as to allow for a more accurate comparison to other filtered images and data stored in a calcium scoring database which have a similar reference spatial resolution.

In calcium scoring a patient, a supine subject is typically asked to hold their breath and multiple scans can be performed while the table moves the subject through the x-ray beam. In an electron beam CT scanner (EBCT) an ECG signal is used to trigger the scanner acquisition at desired points in the cardiac cycle, with or without overlap of slices (prospective gating). In a helical CT scanner, there typically is a higher degree of overlap, and the scanner may be triggered so as to obtain data only during certain parts of the cardiac cycle (which requires that images be reconstructed from data obtained during different heartbeats, and in multi-detector scanners, from different detector rows), or the scanner can operate continuously and the data will be reconstructed and sorted afterwards (retrospective gating). One exemplary retrospective gating methodology is described in co-pending Provisional Patent Application Ser. No. 60/306,311 filed Jul. 17, 2001, the complete disclosure of which is incorporated herein by reference.

The ability to quantify the amount of calcium in a lesion depends on two major factors. The first factor is the spatial resolution of the image, which can be defined as a full width at half maximum or "FWHM" of the device. The full width half maximum is the full width of a spectral band at a height equal to half of the height at the band maximum. The FWHM of the CT scanners will generally be between approximately 1 mm and 2 mm FWHM. It should be appreciated however, that the present invention is equally applicable to CT scanners and other imaging devices having a FWHM outside of this range, however, it is generally not desirable to have large FWHM and blurred images.

The second factor is the signal-to-noise ratio of the procedure. Spatial resolution, in turn depends on machine intrinsic factors (in-plane resolution, slice thickness and reconstruction algorithms) and on motion, both from the table and the patient's heart.

To understand how the spatial resolution and signal-to-noise ratio affect the scoring of the calcium burden, one must understand the Agatston Score. The Agatston Score includes the product of two numbers, a weighting factor derived from the peak intensity observed in a lesion and the area of the lesion in each slice it occupies, computed from the number of voxels that are above a given Hounsefield Units (HU) threshold and are connected together in-plane and if desired, across slices. A more complete description of the Agatston Score and analysis of CT images are described in Agatston A. S. et al, "Quantification of Coronary Artery Calcium Using Ultrafast Computed Tomography," J. Am. Coll. Cardiology 1990; 15:827–832, the complete disclosure of which is incorporated herein by reference.

Table 1 illustrates a weighting factor table based on the peak intensity observed in a lesion:

TABLE 1

| Agatston Weighting Factor | |
|---|---|
| PEAK INTENSITY in HU | WEIGHTING FACTOR |
| Under threshold | 0 |
| Threshold-199 | 1 |
| 200–299 | 2 |
| 300–399 | 3 |
| 400 and higher | 4 |

The threshold for an EBCT is typically about 130 HU, and for helical scanners it is usually suggested to be about 90 HU. The value of 130 for EBCT represents a value that is about 2 standard deviations above the general value of vascular tissue density. The value of 90 suggested for the helical scanners resulted from one study and was chosen to correlate to results with EBCT. From Table 1 it is noted that in certain ranges the Agatston Score are very sensitive to the value of the single highest signal pixel in the lesion, and in other ranges, the score is very insensitive. For example, if the scanner has a noise level of 10 HU, a peak value of 350 HU is not likely to be affected by noise, but one of 395 HU may result in a weighting factor of 4 almost as often as one of 3. Factors other than noise affect the weighting factor. CT scanners have a finite spatial resolution generally on the order of one millimeter.

As shown in FIG. 1, for a 1 mm-diameter cylindrical lesion that has its long axis span the slice, a 1 mm FWHM (Full Width Half Maximum) resolution will drop the peak intensity of the lesion to half, and a ±10% variation in resolution will result in a peak intensity range that will vary by 28%. The second effect from finite spatial resolution is that the area over which the signal extends increases as the resolution worsens. The total signal remains constant, but will be spread over a larger area. A scanner with poorer resolution will drop peak intensity and spread the signal over a larger volume. If the change in peak intensity does not change the weighting factor, then the Agatston Score will go up for poorer resolution, but if the peak drops through one of the thresholds, then the score could go up or down due to poorer spatial resolution.

In a noiseless situation, all of the signal can be extracted, but in the presence of noise, some signal is lost in the noise. For the example above, Table 2 shows the resulting peak intensity, lesion volume, Agatston Score and total integrated signal for a 1 mm-diameter cylindrical lesion.

TABLE 2

Effects of Threshold on Scoring

| THRESHOLD (HU) | VOLUME (cu mm) | AGATSTON | INTEGRAL (HU × volume) |
|---|---|---|---|
| 130 | 10.38 | 14 | 5110 |
| 90 | 12.46 | 16.61 | 5333 |
| Percent Change | 16.7% | 16.6% | 4.2% |

Changing the threshold from 130 HU to 90 HU changes the lesion volume and Agatston Score by 17% for this particular lesion, and the integral by a much smaller 4%. The lower the noise from the scanner, the closer one can come to capturing all of the available signal, and therefore, the less sensitive to spatial resolution changes. Everything described herein regarding intrinsic scanner spatial resolution also applies to sensitivity to motion. The speed of the scanner and the methodology used to acquire and reconstruct images can also affect spatial resolution (and artifacts that may mimic lesions) and consequently affect the Agatston Scores. If a scanner is slower so that there is more signal blurring, but has lower noise, lowering the threshold will compensate (in part, or even overcompensate) for the loss of the peak signal. Noise, however, is both stochastic and structured, and that motion can introduce structured noise that can exceed the scanner's stochastic noise.

The methods and systems of the present invention improves consistency in calcium scoring by filtering, or otherwise adjusting the spatial resolution of the images obtained by the imaging device to a reference spatial resolution so as to allow for a more consistent and accurate calculation of the Agatston Score and a better comparison to other images (and Agatston Scores) in a calcium scoring database.

Figure 2:
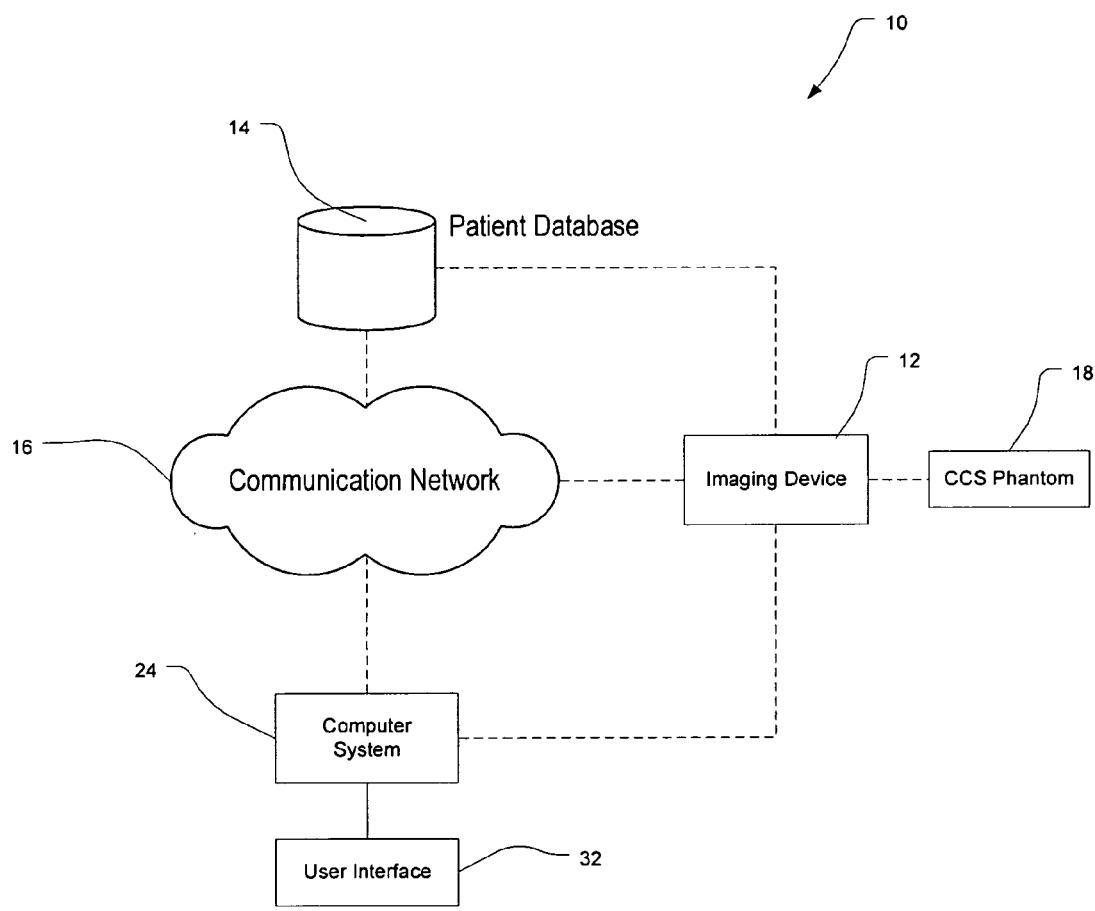
FIG. 2 illustrates an exemplary system of the present invention.

FIG. 2 illustrates a system 10 incorporating aspects of the present invention. System 10 generally includes an imaging device 12 that can obtain an image dataset of the patient. A phantom 18 can be periodically imaged by imaging device 12 to provide information about the imaging performance (such as the spatial resolution) of imaging device 12. Imaging device 12 can deliver a digitized dataset to a computer system 24 and a memory, server, or database 14 via a communication network 16.

Imaging device 12 can be a spiral or electron beam CT scanner, an x-ray unit, or other conventional imaging devices that can obtain an image dataset. In exemplary embodiments, the imaging devices produce a Digital Imaging and Communications in Medicine (DICOM) format file that contains a header (which stores information about the patient's name, the type of scan, image dimensions, etc) and the image data in three dimensions. Electrocardiograph leads (not shown) can be attached to the patient and an electron beam imaging device to trigger the imaging device to start the image capture process.

Imaging device 12 can be coupled to database 14 through communication network 16 so as to store the image dataset (s) and the other patient and imaging information. Communication network 16 may include hardwire links, optical links, satellite or other wireless communications links, wave propagation links, or any other mechanisms for communication of information. Various communication protocols may be used to facilitate communication between the various systems shown in FIG. 2. These communication protocols may include TCP/IP protocol, HTTP protocols, extensible markup language (XML), wireless application protocol (WAP), vendor-specific protocols, customized protocols, and others. Communication links may also represent communication paths through interconnected computer networks, intermediary devices, switches, routers, other communication links, and the like. The computer networks may include the Internet, a local area network (LAN), a wide area network (WAN), wireless networks, intranets, private networks, public networks, switched networks, and the like.

Computer system 24 of the present invention can be operably connected to the imaging device 12 and/or patient database 14 to obtain and process the appropriate imaging and patient data. Computer system 24 can take the form of a computer system running one or more software packages which can access the database, analyze the image datasets, filter the spatial resolution of the imaging device, and the like.

Figure 3:
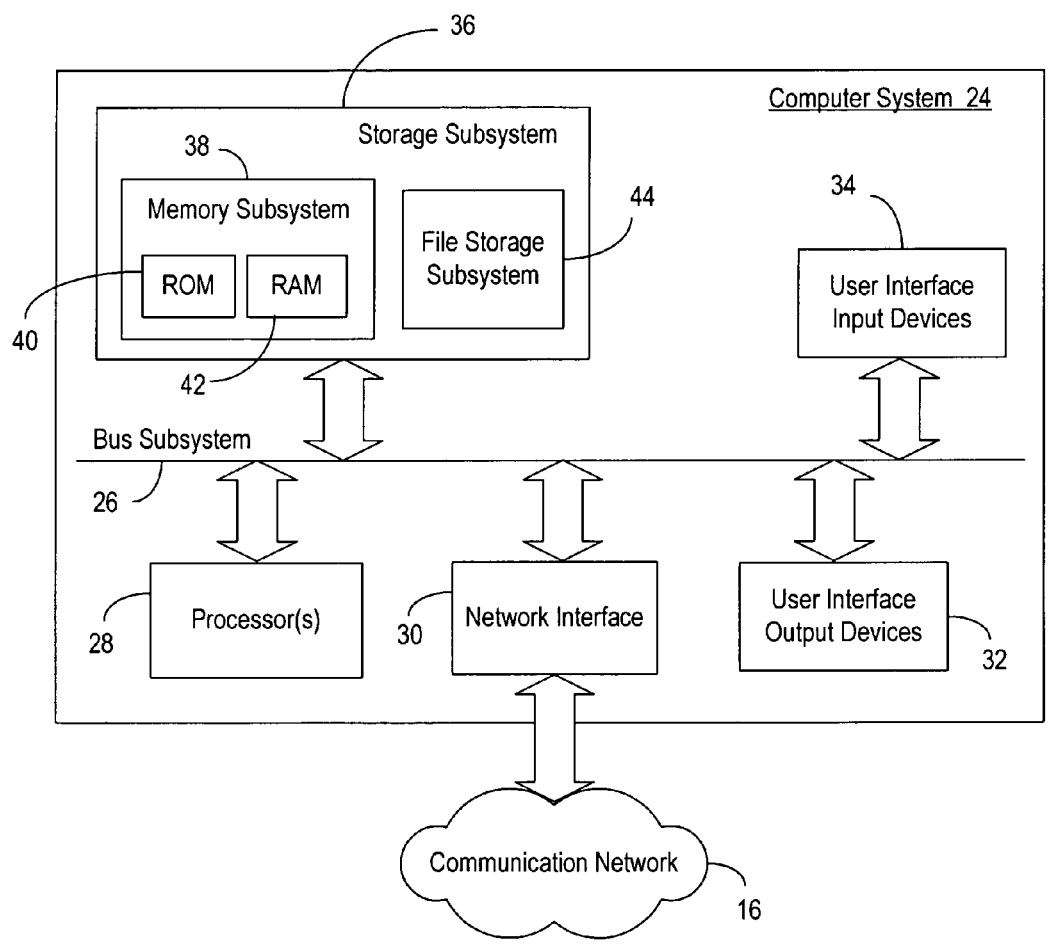
FIG. 3 illustrates an exemplary computer system of the present invention.

FIG. 3 is a simplified block diagram of an exemplary computer system 24 incorporating the software of the present invention. Computer system 24 typically includes at least one processor 28 which communicates with a number of peripheral devices via a bus subsystem 26. These peripheral devices may include a storage subsystem 36, comprising a memory subsystem 38 and a file storage subsystem 44, user interface input devices 34, user interface output devices 32, and a network interface subsystem 30. Network interface subsystem 30 provides an interface to outside networks, including an interface to communication network 16, and is coupled via communication network 16 to corresponding interface devices in other computer systems.

User interface input devices 34 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. In general, use of the term "input device" is intended to include a variety of devices and ways to input information into computer system 24 or onto computer network 16.

User interface output devices 32 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide non-visual display such as via audio output devices. In general, use of the term "output device" is intended to include a variety of devices and ways to output information from computer system 24 to a user or to another machine or computer system.

Storage subsystem 36 stores the basic programming and data construct modules that provide the filtering and calibration functionality of the various embodiments of the present invention. For example, the database and modules implementing the functionality of the present invention may be stored in storage subsystem 36. These software modules are generally executed by processor 28. In a distributed environment, the software modules may be stored on a plurality of computer systems and executed by processors of the plurality of computer systems. Storage subsystem 36 typically comprises memory subsystem 38 and file storage subsystem 44.

Memory subsystem 38 typically includes a number of memories including a main random access memory (RAM) 42 for storage of instructions and data during program execution and a read only memory (ROM) 40 in which fixed instructions are stored. File storage subsystem 44 provides persistent (non-volatile) storage for program and data files, and may include a hard disk drive, a floppy disk drive along with associated removable media, a Compact Digital Read Only Memory (CD-ROM) drive, a CD-R, CD-RW drive, an optical drive, or removable media cartridges. One or more of the drives may be located at remote locations on other connected computers at other sites coupled to communication network 16. The databases and modules implementing the functionality of the present invention may also be stored by file storage subsystem 44.

Bus subsystem 26 provides a mechanism for letting the various components and subsystems of computer system 24 communicate with each other as intended. The various subsystems and components of computer system 24 need not be at the same physical location but may be distributed at various locations within distributed network 10. Although bus subsystem 26 is shown schematically as a single bus, alternate embodiments of the bus subsystem may utilize multiple busses.

Computer system 24 itself can be of varying types including a personal computer, a portable computer, a workstation, a computer terminal, a network computer, a module in the imaging unit, a mainframe, or any other data processing system. Due to the ever-changing nature of computers and networks, the description of computer system 24 depicted in FIG. 2 is intended only as a specific example for purposes of illustrating the preferred embodiment of the present invention. Many other configurations of computer system 24 are possible having more or less components than the computer system depicted in FIG. 2.

A calibration module (not shown) can incorporate the methods of the present invention described herein as software code. The calibration module can be stored in storage subsystem 36 and run by processor 28 to analyze the spatial resolution of the image of a phantom and to generate a filtering algorithm to adjust the spatial resolution of images taken thereafter with imaging device 12 to a reference spatial resolution.

Database 14 of the present invention can include DICOM files, patient information, and the corresponding calcium scores. Storage of the patient's calcium scores, (most commonly with the Agatston scale), age, and gender of the individual can be used to rank each individual patient against his or her age-matched cohorts whose information is stored in the database. Unlike conventional calcium scoring databases, the database of the present invention can be used to compare images and calcium scoring results taken from a plurality of different CT scanners since the images and information stored in the database will have been filtered (typically to the same reference spatial resolution) before entering the images and calcium scoring information into the database.

In exemplary embodiments, a filtering algorithm is applied to the image dataset before the images are calcium scored or entered into database 14. Consequently, the information about the filtered images stored in the database all are based on the images that has a spatial resolution that substantially matches a reference resolution. Unlike conventional databases, because all of the images that are calcium scored are at substantially the same spatial resolution the is a greater assurance of patient database consistency of calcium scores thus obtained. Thus, images taken from different CT scanners (both helical and electron beam) from different areas in the world can upload calcium scoring information into the database. Unlike the local databases that use only a single CT scanner, because of the different CT scanners that can image and calcium score people of different ages, ethnicity, social background, a broader-based study of calcium scoring can be developed and used to analyze calcium scores.

Databases 14 of the present invention may or may not store the original images and filtered images. For convenience, in preferred embodiments only the calcium scores are stored in database 14 and the images are stored only at the imaging site. In other embodiments, however, it is possible to store both the images and the calcium scores in database 14 of the present invention.

Imaging device 12 of the present invention is typically an electron beam or helical CT scanner or an x-ray scanner that produces images in the DICOM file format. It should be appreciated, however, that other imaging technologies (e.g., MRI scanners, nuclear imaging, and the like) and other file formats can, in principle provide the calcium scoring images of the present invention, but are not generally accepted for such purposes at this time.

The phantom and calibration module of the present invention can be used to help generate the filtering algorithm that corrects the spatial resolution of the images obtained with the imaging device so as to allow for a comparison of other filtered or original images having substantially the same spatial resolution.

Figure 4:
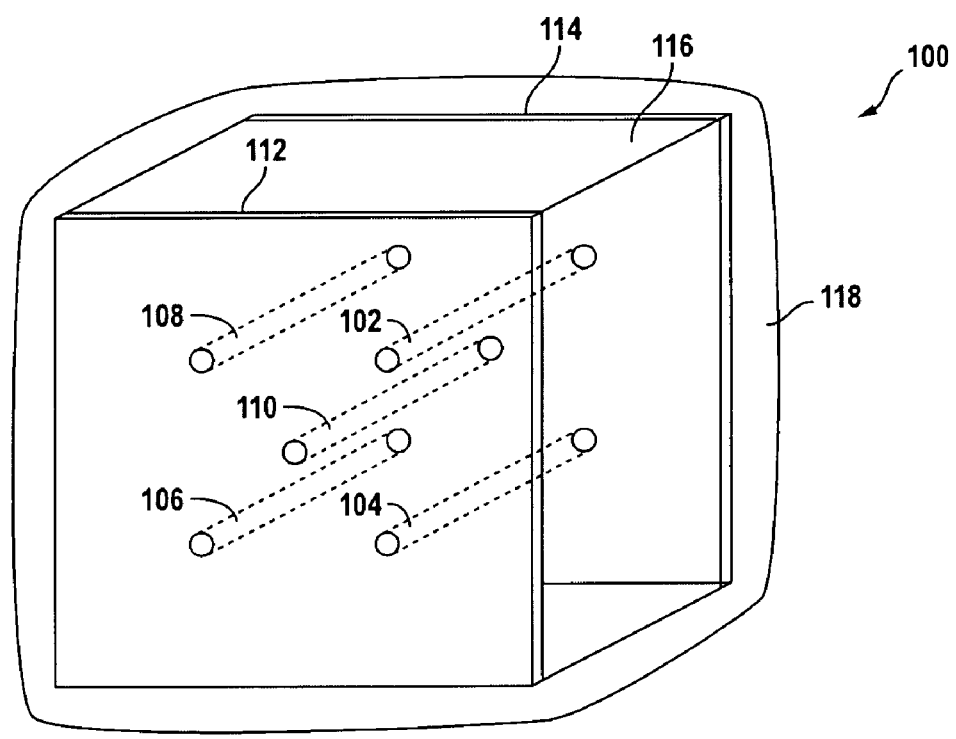
FIG. 4 is a perspective view of an exemplary phantom of the present invention.

One exemplary phantom 100 that allows for the measurement of resolution and noise of an imaging device is shown in FIG. 4. The exemplary phantom 100 has a plurality of elongate wires 102, 104, 106, 108, 110. Typically the wires are comprised of aluminum or hydroxy apatite. Aluminum's electron density, HU~2500 is about two times as large as hydroxy apatite.

The phantoms can be used to simulate "lesions" that can be scored and from which peak intensity, volume at a given threshold, and noise can be measured. While such a phantom cannot account for the complexities introduced by motion, the imaging and scoring of the phantom can assure on a regular basis that the scanners themselves are operating consistently and allows different units to be calibrated against each other.

It should be appreciated, however, that while aluminum and hydroxy apatite are some exemplary materials for the phantoms, that the phantoms of the present invention can be composed of different materials, such as aluminum alloys, titanium, boron carbide and the like. Aluminum is chosen because wires of consistent diameter can be obtained in a convenient, reliable, and cost-effective manner. Similarly, the phantom may consist of air-filled holes of different diameter formed in a solid matrix such as plastic or epoxy.

Figure 5:
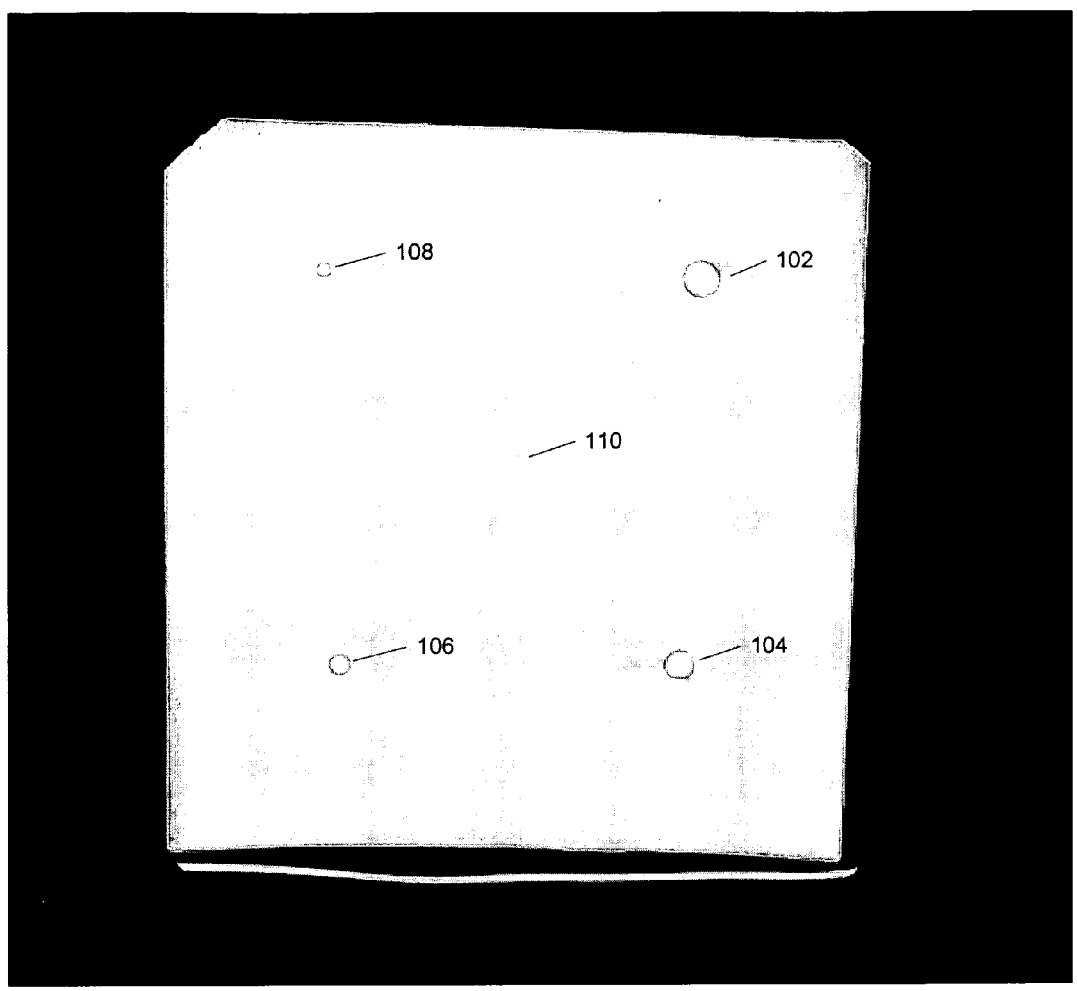
FIG. 5 is an image of an exemplary phantom of the present invention.

FIG. 5 illustrates an exemplary phantom 100 which comprises five aluminum wires 102, 104, 106, 108, 110 having varying dimensions. In the illustrated embodiment wire 102 is a conductor size 8 AWG (American Wire Gauge Size) having a diameter of 3.264 mm (128.5 mils) and an area of 8.366 mm$^2$ (16510 CM [circular mils]), wire 104 is a conductor size 12 AWG having a diameter of 2.053 mm (80.8 mil) and an area of 3.309 mm$^2$ (6530 CM), wire 106 is a conductor size 18 AWG having a diameter of 1.024 mm (40.3 mils) and an area of 0.823 mm$^2$ (1624 CM), wire 108 is a conductor size 24 AWG having a diameter of 0.511 mm (20.1 mils) and an area of 0.205 mm$^2$ (404 CM), and wire 110 is a conductor size 28 AWG having a diameter of 0.321 mm (12.6 mils) and an area of 0.081 mm$^2$ (159.8 CM). It should be appreciated however, that the wires of the phantoms of the present invention are not limited to such dimensions and that a different number of wires, having other dimensions or materials can be used in the phantom 100 of the present invention.

Typically, the wires are approximately 1-inch long and are embedded in a spaced configuration in a low density matrix to position the wire. In exemplary embodiments, the low density matrix include plastic support structures 112, 114 at each end of the wires and water 116 in the space between plastic support structures. Water 116 and plastic support structures 112, 114 can be further encased in a watertight covering 118.

Water 116 is used in the phantom 100 because the tissues in which calcium is found are water-like when viewed in x-ray CT and because water is a consistent medium, convenient, non-toxic and minimally hazardous. It should be appreciated, however, that other liquids or materials having similar or dissimilar electron densities can be used.

Generally, to measure the spatial resolution as a full width half medium or FWHM, at least one of the wires should have a diameter that is less than approximately 3.0 times as large as the FWHM of the image device. More preferably, the wires should have a diameter between approximately 0.1 times as large as the FWHM and 3.0 times as large as the FWHM. If the diameter of the wire is too large, there will be little or no information on the FWHM in the image. Conversely, if the diameter of the wire is too small, the signal will be lost in the noise. Thus, to improve the information of the FWHM of the image, the phantoms of the present invention use wires having varying diameters between approximately 0.1 times as large as the FWHM and 3.0 times as large as the FWHM range found in the imaging devices being used. For much smaller wires, the signal became too weak to score with current technology CT scanners. As the diameter gets large, information as to the FWHM as computed by the exemplary embodiment becomes scarce. A very large test object of high absorption may also introduce artifacts. Conversely, such a large object can be very useful for determining the peak intensity of the signal at the wire for the case of FWHM=0, or $C_o$, since the dependence on FWHM becomes negligible. Nothing in the methodology of the present invention precludes the use of a large object. Furthermore, it is noted that the FWHM can be obtained from other tests, such as analysis of the response of the scanner to an edge between high and low density objects (edge response function), or the like.

Figure 6A:
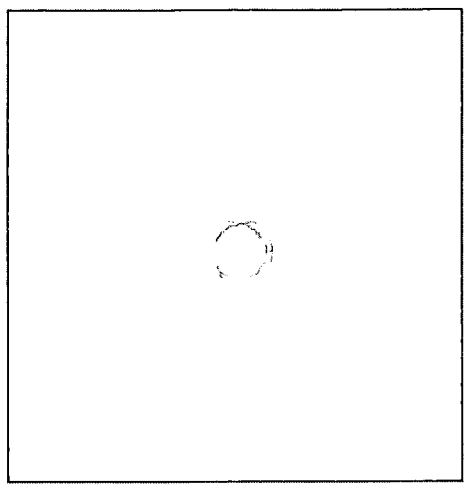
FIG. 6A is an image of one wire of the phantom obtained with a spatial resolution of 1.3 mm FWHM.
Figure 6B:
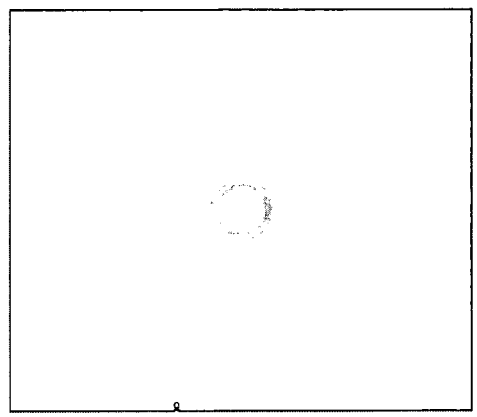
FIG. 6B is a filtered image of the wire in the phantom in which the FWHM is filtered to 1.7 mm
Figure 6C:
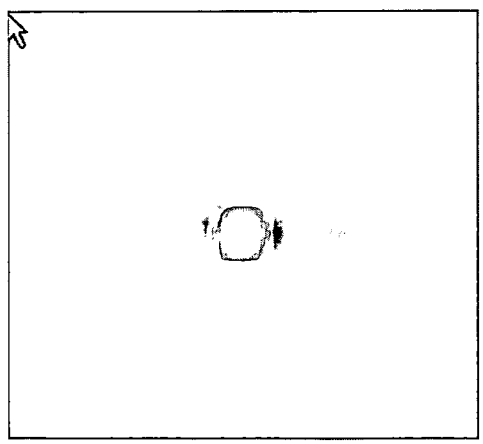
FIG. 6C is a filtered image of the wire in which the FWHM is filtered to 0.9 mm.

FIG. 6A is a magnified image of a 1 mm diameter wire having a spatial resolution of approximately 1.3 mm FWHM. FIG. 6B is a magnified image of the same wire corrected to a spatial resolution of 1.7 mm FWHM. FIG. 6C is a magnified image of the same wire corrected to a sharpened spatial resolution of 0.9 mm FWHM.

Figure 7:
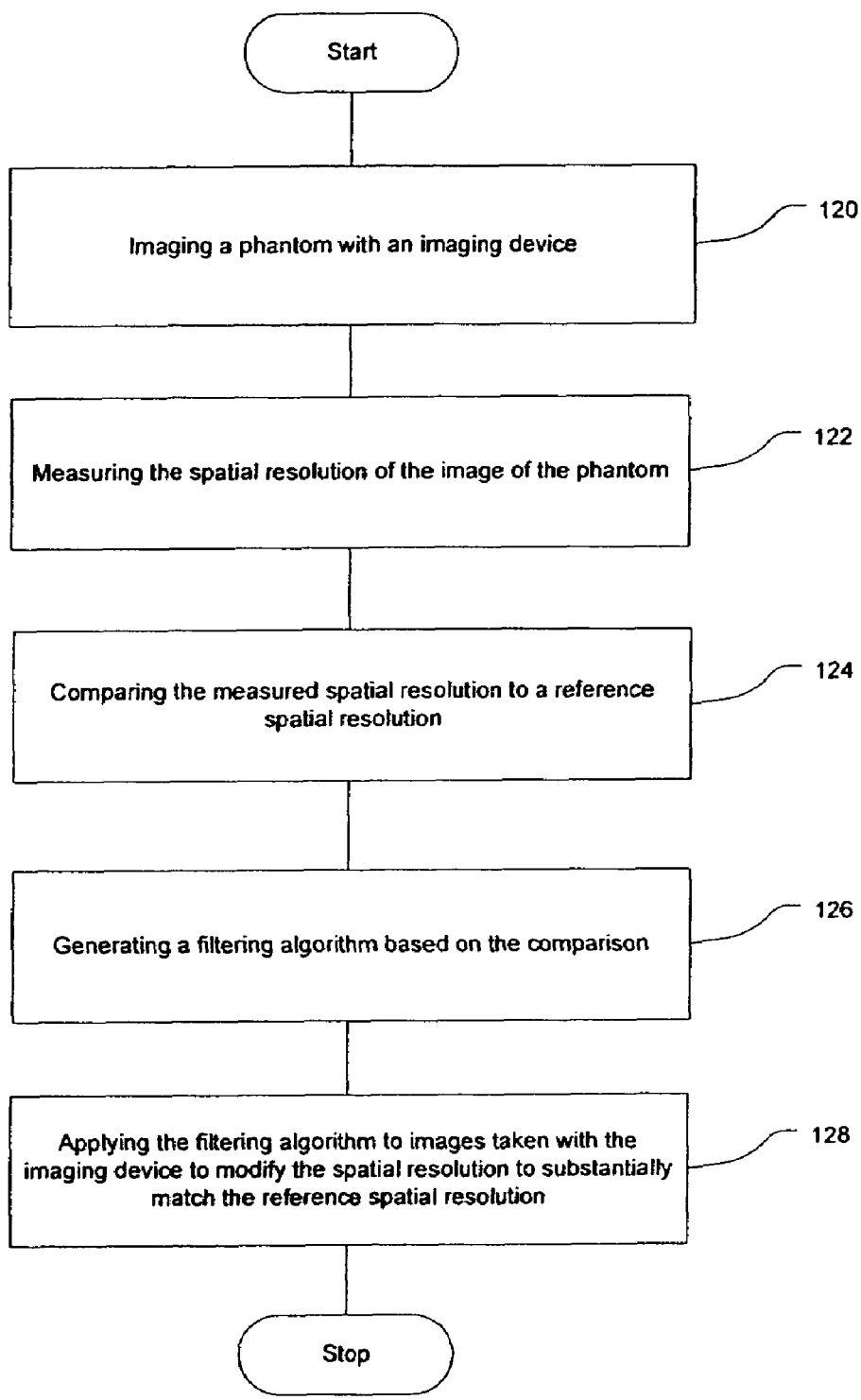
FIG. 7 schematically illustrates an exemplary method of the present invention.

As shown schematically in FIG. 7, on a periodic basis, phantom 100 is imaged in the target CT scanner with the same protocol as that used for calcium scoring, as described above. (Step 120). (See FIG. 5 which illustrates a CT image of a slice of a calcium scoring calibration phantom 100 in which all five cross sections of the wires are illustrated).

From the imaging of the phantom image, the spatial resolution (FWHM) of the CT scanner can be determined. (Step 122). The measured FWHM can then be compared to a reference FWHM. (Step 124). Based on the comparison of the measured FWHM to the reference FWHM, a filtering algorithm can be generated (Step 126) and applied to the images of the CT scanner that are thereafter obtained by the CT scanner. The filtering algorithm can adjust the image data so that the measured FWHM of the obtained images becomes substantially equal to the reference FWHM. (Step 128). Thereafter, the imaging device can be used to calcium score patients in which the resultant images will have the reference FWHM (not shown).

In general, the filtering algorithm substantially removes the effect of the resolution of the image. For example if the image has a 1.3 mm resolution, but wanted 1.5 mm resolution, the filtering algorithm would ideally first sharpen from 1.3 mm down to approximately 0 mm and then smooth to 1.5 mm resolution. Conversely, if it is desired to adjust or sharpen the resolution from 1.3 mm to 1.0 mm, the filtering algorithm would first sharpen to approximately 0 mm and then blur to 1.0 mm resolution. In theory, the order of these operations is interchangeable with no effect on the result. In practice, the filtering algorithm can combine these two processes into one operation done at the same time to avoid possible problems from machine precision.

In exemplary embodiments, to image the phantom 120, the operator opens the calibration module of the software of the present invention, imports the DICOM study that contains the images of phantom 100, and selects a slice for measurement. The calibration module can be configured to automatically locate the wires and perform the above calculations for the selected slice and its two neighboring or more slices. The calibration module (or other software module) can also provide an Agatston score and volume score for each slice as a quality assurance benefit to the operator of the scanner and its maintenance personnel.

Such data can then be stored in database 14 that stores the study date, study DICOM header information, $C_o$ and FWHM for each slice, and the average of the two parameters ($C_o$ and FWHM) for the number of slices measured, as well as the peak intensities C for the wires and the individual and Average Agatston scores and volume scores.

For a selected parameter, database 14 can be queried to display the last measurement, to show a table of the last N measurements, or to show a graph of the last N measurements to inform the operator of the changes of spatial resolution of the imaging device over time.

For step 124, the measured FWHM can be compared by the software to a reference FWHM(ref) which may be an arbitrary value to which various centers agree by consensus, it may be the FWHM at the start of operation of a CT scanner, it may be the FWHM with which the reference database was acquired, or any other appropriate value. The software of the present invention can then generate a filtering algorithm based on the comparison of the measured FWHM of the phantom with the reference FWHM.

One exemplary method of measuring the spatial resolution that can be incorporated by the method and software of the present invention will now be described. The spatial resolution of the phantom 100 can be determined by using the following expressions:

$$C=C_o(1-\exp(-0.69D^2/FWHM^2))$$

and $$FWHM=0.83 \times D/\sqrt{\log(C_o/(C_o-C))},$$

where: D is the diameter of the wire

C is the peak intensity of the signal at the wire $C_o$ is a constant that can be found from imaging 2 or more wires and measuring C for each. $C_o$ represents the peak intensity of the signal at the wire for the case of FWHM=0.

and log is the natural logarithm of the expression in parenthesis

A more complete description of these equations and their use is described in Shosa D. W. and Kaufman L., "Methodology For Evaluation of Diagnostic Imaging Instrumentation," Phys. Med. Biol. 26: 101, 1981; "In Progress in Nuclear Medicine, Neuro-Nuclear Medicine," edited by O. Juge and A Donath: S Karger, A. G., Basel, Switzerland, 1981; Kaufman, L. and Shosa, D. W., "Quantitative Characterization of Signal-to-Noise Ratios in Diagnostic Imaging Instrumentation," page 1; Kaufman L. and Shosa D. W., "Generalized Methodology for the Comparison of Diagnostic Imaging Instrumentation," AFIPS Press 49: 445, 1980; and Shosa D. W., Kaufman L., Hattner R. S. and O'Connell W., "Measurement of the Texture Contribution to Image Noise in Scintigrams," Applications of Optical Instrumentation in Medicine VIII, SPIE 233: 134, 1980, the complete disclosures of which are incorporated herein by reference.

In the above equation, the measurement of the peak intensity of the wires (C) can be automatic or the operator can select the wires with conventional software tools. The wire diameter (D) is known. The two unknowns are FWHM and $C_o$. The software of the present invention can minimize the weighted differences between individual values of FWHM and the average FWHM for the five wires to find the best fit. An exemplary fitting algorithm is described below.

Under the assumption that the underlying mechanism determining the image intensity results from a Gaussian point spread function, an image intensity, C, can be defined by:

$$C=I(s)=C_o(1-\exp(-\log(2)(D/f)^2)),$$

where D is the wire diameter, f is the FWHM of the point spread function, and $C_o$ is the signal intensity for FWHM=0 or where D>>FWHM.

The data as measured in an image will have an additional contribution from noise and artifact, which can approximate both effects as an additive uncorrelated noise process that contributes on average equally to each data point.

Under the further assumption that the noise process is Gaussian, one can find the most likely values of $C_o$ and f given a set of measured image points by calculating the values of $C_o$ and f that minimizes the $\chi^2$ sum of the differences of the observed data values and the model values, where:

$$\chi^2=\Sigma(I_i-I(D_i))^2$$

The sum is performed for all values of the subscripted variable, i, which represents all of the acquired data. In further sums, the sum is performed over the subscripted roman letter index. For a further description of $\chi^2$, see Stuart L. Meyer, "Data Analysis for Scientists and Engineers", John Wiley & Sons, New York, 1975.

This problem can be solved through a variety of means. Some approaches use methods for nonlinear optimization, such as a simplex search, conjugate gradient search, or simulated annealing techniques. These methods are well understood but generally require computationally intensive techniques to be done automatically. Methods of finding a best-fit solution which incorporates knowledge of the fitting function will generally be faster and give more consistently reliable results.

The methods used in the present invention assumes that there is an approximate value for one of the parameters and then uses a simple formula to calculate the other so as to minimize $\chi^2$ given that assumption. The first parameter can be varied to find a best value for it which gives the overall best fit to the data. Unlike other methods, this requires only a one parameter search which is generally much easier and faster than a two parameter search.

Another method is to estimate $C_o$ and manipulate the expression for the signal intensity and derive an expression for f in terms of the other parameters $$f=D_i(\log(2)/\log((C_o-I(D_i))/C_o))^{1/2}$$

This expression is a simplification of the previous expression since it linearizes the relationship between the known parameters and the unknown parameters. The methods of the present invention can then fit the one remaining unknown, f, to the set of intensities. The best value for f for a set of image intensities can be expressed using a linear fit expression or another method, such as finding the one that minimizes the variation in f from the mean. If the data were perfect then the proper value of $C_o$ the right side of this expression would be constant for each of the observed data points. For real data, however, the best estimate for $C_o$ is assumed to be the value that minimizes the variation. Performing this fit, however, will not necessarily result in the best overall minimization of $\chi^2$. Since a logarithm of data is taken, the value of $C_o$ that produces the least variation in f will not necessarily be the one that minimizes $\chi^2$.

Another exemplary approach to fitting the data is to assume an estimate for f. Under this assumption the value for $C_o$ which minimizes $\chi^2$ can be calculated by a formula for linear fitting. This value is:

$$C_o=\Sigma(I_i(1-\exp(-\log(2)(D_i/f)^2)))/\Sigma(1-\exp(-\log(2)(D_j/f)^2))^2$$

If an estimate is substituted for $C_o$ in the expression for $\chi^2$ the expression which is to be minimized provides:

$$\Sigma I_i^2-(\Sigma(I_i(1-\exp(-\log(2)(D_i/f)^2))))^2/\Sigma(1-\exp(-\log(2)(D_j/f)^2))^2$$

The first sum in the expression is the sum over the observed data points and will not be affected by varying f. The second term, since it enters with a negative sign, is the one that is to be maximized. The problem of minimizing the two parameter function is reduced to a one parameter search.

Rather than search for a maximum of this expression, an expression can be derived for the derivative of this with respect to f. Finding the zero of the derivative yields the best fit value for f. Numerically finding the zero of a function is much easier than finding a maximum—there are numerous techniques for finding zero which converge much more rapidly than finding a maximum Let $a=\log(2)/f^2$ and $s=D^2$. The expression that is used to find the zero for is:

$$d\chi^2/da = 2\Sigma s_i I_i \exp(-as_i)\Sigma I_j(1-\exp(-as_j))/\Sigma(1-\exp(-as_k))^2 - 2\Sigma s_i \exp(-as_i)(1-\exp(-as_i))(\Sigma I_j(1-\exp(-as_j)))^2/(\Sigma(1-\exp(-as_k))^2)^2$$

Finding the zero of this function requires a start with an initial estimate of f, then iterate using Newton's method to find the zero of this function. This function can be shown to have at least one zero and in all cases examined the zero is unique. Using Newton's method generally finds the zero to machine accuracy in 5 or 6 iterations.

It can be appreciated that the phantom need not be of cylindrical objects spanning the slice. For instance, spherical objects could be used, which would require a more complex formulation as described in Shosa D. W. and Kaufman L., "Methodology For Evaluation of Diagnostic Imaging Instrumentation," Phys. Med. Biol. 26: 101, 1981. A major disadvantage of using an object that is not uniform along the slice direction is that in x-ray CT, slices have non-uniform profiles, and these profiles vary depending on how the scanner is utilized. Without an independent measurement of the profile, and more complicated analysis, a reliable measure of the spatial resolution would not be obtained.

After the image parameters f and $C_o$ are found, these parameters are used to correct the image to a standard or reference resolution and intensity values. If the reference resolution is larger than the measured resolution, this requires that a smoothing function be applied to the image data, such as the following convolution kernel:

$$\exp(-\log(2)(x^2+y^2)/f^2)$$

One exemplary method of performing the convolution is to Fourier transform the image, multiply by the Fourier transform of the smoothing kernel and inverse Fourier transforming. Since the smoothing kernel has a Gaussian form, it is a product of a Gaussian of x and y separately. One preferred method for implementing such a filter is to Fourier transform one row of the image in the x direction, multiply by the Fourier transform of filter in x, then inverse Fourier transform. After one row has been transformed, the operation is individually applied to each of the rows until all of the rows have been transformed. After the rows have been transformed, the operation is applied to one column at a time in the y direction until all of the columns are transformed. By filtering the image one row and one column at a time, allocation of memory to the filtering procedure can be reduced.

The Fourier transform of the convolution kernel is also Gaussian. For a smoothing operation, it is exponentially decreasing as it moves away from the center of Fourier space.

If the reference resolution is smaller than the measured image resolution, then the image needs to be sharpened. While this is formally identical to the proceeding case, it is complicated by the presence of noise in an image. Unlike the case of the smoothing operation, sharpening the image requires that multiplication of the Fourier transform of each row and column of the image by an exponentially increasing function.

The point at which the sharpening operation introduces an unacceptable level of artifact can be estimated. If the image signal to noise is 100:1 and the object occupies 50% of the field of view in one direction, then the ratio of the peak signal to the mean noise in the Fourier domain for an image on a 512 pixel matrix is approximately 11,000 to 1. When the exponential increase of the Fourier transform is larger than this number, a doubling of the noise in a sharpened image will occur. If the magnitude of the sharpening filter is much larger than this, the level of artifact introduced by the sharpening will increase and be unacceptable.

To counteract the level of artifact introduced by sharpening, the sharpening filter can be apodized or flattened by tapering of the sharpening filter so that it never exceeds the target value of 10,000 (a rounding of the 11,000:1 ratio). There are many known methods of introducing such an apodization factor and will depend on the desired appearance.

One apodization scheme is to include a factor of cosine in the exponent of the filter in such a way that the filter never exceeds 10,000 and approaches 1 at the edge of Fourier space.

Filtering in the present invention can also be carried out by multiplying the spatial signal distribution values with a filtering or correction algorithm to each data point of the image by a weight that is obtained from a particular algorithm, or otherwise varying the individual values of the data point in a matter determined by an algorithm. Some algorithms that can be used are Fourier interpolation filters, cubic filters, Gaussian filters, maximum likelihood estimators, Bayesian estimators and the like.

In exemplary embodiments, the filters can smooth and/or sharpen the images to provide the desired spatial resolution in the image. In one exemplary embodiment, to filter the spatial resolution to the desired spatial resolution, first Fourier transformation is applied to the acquired image. A frequency space two-dimensional data of the acquired image is filtered. A second Fourier transformation is performed to obtain an image having the reference spatial resolution.

In one embodiment, which is mathematically similar to the above, but uses less memory in computer system is as follows. First, a Fourier Transform is applied to a single line in the acquired image.

The frequency space one-dimensional data of the acquired image is filtered. A second Fourier transformation is performed to obtain a line in the image comprising the reference spatial resolution. Such a process is repeated on every parallel line in the image and then on every line that is orthogonal to the first line to obtain an image comprising the reference spatial resolution.

In other filtering methods of the present invention, the absorption data from the detectors of the CT scanner can be filtered before reconstruction yields the image. In such methods, a signal distribution along the CT detectors is multiplied by a set of weights so as to yield the reference spatial resolution.

In yet another filtering method, filtering can be carried out by back projection reconstruction, in which absorption data or profiles of the image are multiplied by a function. In such back projection reconstruction, each detector's modified signal is traced back to the source. At each pixel in the image, the ray provides a weight, in which the weights are added up to obtain the image.

The following examples are meant to show some results from the present invention. It should be appreciated that such results are merely examples, and should not be construed to limit the present invention in any way.

For lesions that are less than 5 mm in dimension, the scanner spatial resolution can be a significant and even dominant factor in Agatston Scores and volume score results. The phantom and software of the present invention can measure spatial resolution and the Hounsefield scale with a precision of 2%.

Applicants have found that small lesions having an individual Agatston Score under 100, that the volume method and Agatston Score are highly reflective of scanner spatial resolution. By changing the spatial resolution of the images, Applicants have found that a more consistent Agatston Score can be measured.

Figure 8:
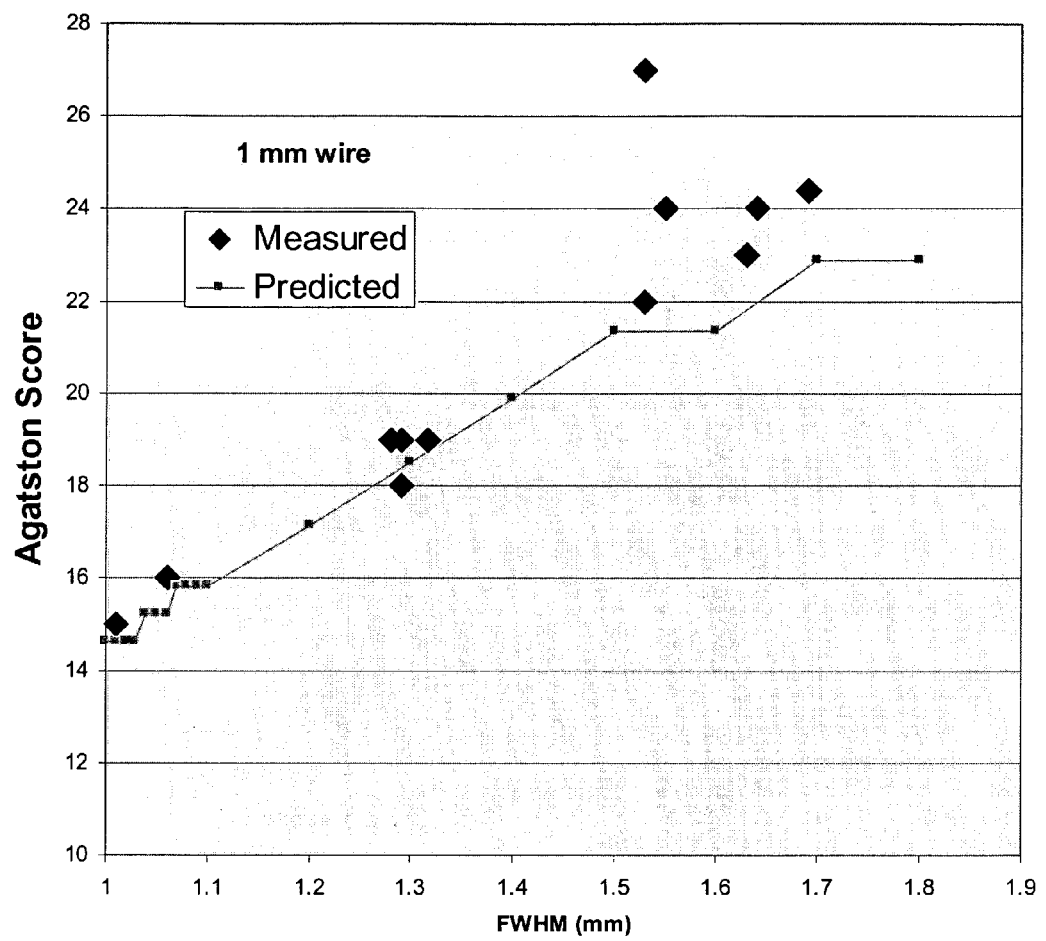
FIG. 8 is a graph comparing a measured and predicted Agatston Score for a 1 mm-diameter wire.

For example, FIG. 8 is a chart illustrating a measured and predicted Agatston score for a 1 mm diameter aluminum wire image using various CT scanners having different spatial resolutions. As shown, as the FWHM increased, the measured Agatston Score increased. Consequently, adjusting the spatial resolution of the images in the database to a fixed value can decrease the variance between the measured and predicted Agatston Score.

Figure 9:
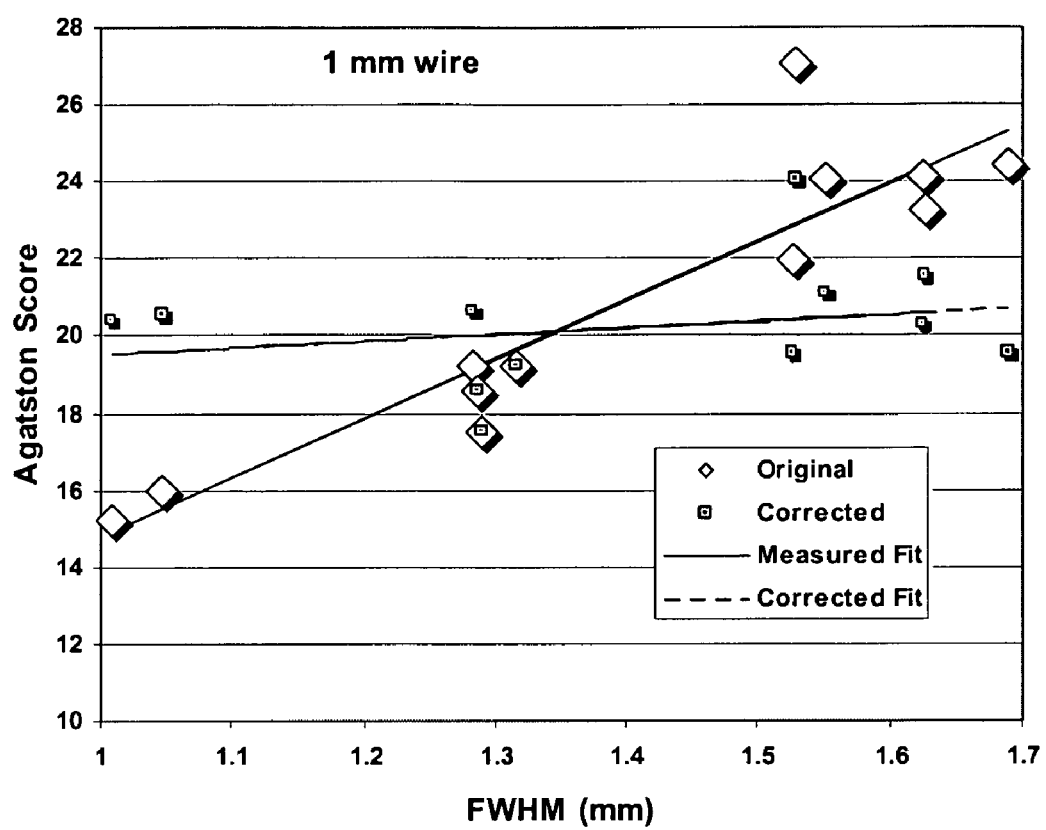
FIG. 9 is a graph illustrating a FWHM and an Agatston Score before and after filtering of the spatial resolution.

The wire phantom of the present invention has been found to yield a spatial resolution to high precision. FIG. 9 illustrates a measured and corrected Agatston Score for a 1 mm-diameter aluminum wire imaged in various CT scanners. As shown, the measured fit of the spatial resolution of the scanner of the wire was highly dependent on the FWHM of the scanner. After the spatial resolution was corrected, the corrected fit of the FWHM of the wire was much more consistent.

In particular, a sampling of 6 scanners with resolution ranging from 1.03–1.69 mm FWHM, Applicants measured Agatston scores of 15 to 27 (20.9±1.1) (mean±standard deviation), and after correction to a reference resolution of 1.3 mm FWHM, the Agatston Score range was reduced to 18 to 24 (20.2±0.5), so that the variance was less than half than before correction (1.1 down to 0.5). Best fits to the data showed originally ranges of 14.9–25.3 (70%) in the Agatston score, reduced to 19.6 to 20.7 (6%) after correction in the range of spatial resolutions measured.

While the following description focuses on adjusting the spatial resolution of CT images to improve the consistency of the measurement of the patient's calcium burden, it should be appreciated, that the methods and systems of the present invention are applicable to the imaging of lung nodules and other small structures of interest by x-ray CT, emission computed tomography (ECT), positron computed tomography (PET) or planar nuclear medicine imaging, where quantitation is needed, and the principles of the present invention may also be applicable to other imaging devices, such as an MRI scanner, x-ray machine, or nuclear imaging.

As will be understood by those of skill in the art, the present invention may be embodied in other specific forms without departing from the essence of the present invention. For example, instead of a calcium burden, the present invention can be used to post process images to improve detection and tracking of lung nodules, prostatic tumors, pituitary carcinomas, or the like.

Additionally, instead of using FWHM as a measure of the spatial resolution, others can be used, such as FW0.1M (full width at one tenth of maximum), MTF (modulation transfer function), edge response function, and so on.

Accordingly, the foregoing description is intended to be illustrative, but not limiting, of the scope of the invention which is set forth in the following claims.

What is claimed is:

1. A method of improving the consistency of coronary calcium scoring, the method comprising:
    imaging a phantom with an imaging device to produce an image of the phantom;
    measuring a spatial resolution from the image of the phantom;
    comparing the measured spatial resolution of the image of the phantom against a reference spatial resolution;
    choosing a filter algorithm, wherein when filter is applied to the phantom image a filtered image is produced having a spatial resolution substantially matching the reference spatial resolution;
    subsequent to choosing a filter algorithm, obtaining an image of a subject;
    applying the filter algorithm to the image of the subject to create a filtered image that has a spatial resolution that substantially matches the reference spatial resolution; and
    computing a coronary calcium score from the filtered image.

2. The method of claim 1 wherein the measured spatial resolution of the image of the phantom and reference spatial resolution are a full width half maximum.

3. The method of claim 1 where the coronary calcium score is an Agatston Score.

4. The method of claim 1 where the coronary calcium score is a volume score.

5. The method of claim 1 where the coronary calcium score is an integral score.

6. The method of claim 1 wherein the calcium scores from the filtered images are input into a database for comparison with scores from other images that comprise the reference spatial resolution.

7. The method of claim 1 wherein measuring is carried out periodically.

8. The method of claim 7 wherein periodically comprises once a day.

9. The method of claim 1 wherein the phantom comprises a plurality of aluminum wires comprising different dimensions embedded in a low density matrix.

10. The method of claim 9 wherein the aluminum wires comprise a diameter that is between approximately 0.1 times the full width half maximum of the imaging device and 3.0 times the full width half maximum of the imaging device.

11. The method of claim 9 wherein measuring the spatial resolution of the phantom comprises measuring a peak signal for each wire.

12. The method of claim 1 wherein comparing is carried out with software.

13. The method of claim 1 wherein the imaging device is a CT scanner and the image of the phantom data comprises absorption data.

14. The method of claim 13 wherein applying the filter algorithm comprises filtering data from detectors of the CT scanner before a reconstruction yields the image.

15. The method of claim 14 wherein applying the filter algorithm comprises multiplying a signal distribution of the images along the detectors by a set of weights that yield the reference spatial resolution.

16. The method of claim 14 where the reconstruction is a back projection.

17. The method of claim 1 wherein the filter algorithm performs at least one of smoothing and sharpening of the acquired images.

18. The method of claim 1 wherein applying the filter algorithm comprises convolving the image with one of a Gaussian filter, Fourier filter, or a cubic filter so that the spatial resolution of the images are adjusted to the reference spatial resolution.

19. The method of claim 1 wherein applying the filter algorithm comprises:
    applying a first Fourier Transform operation to the acquired image;

filtering a frequency space two-dimensional data of the acquired image; and performing a second Fourier Transform operation to obtain an image comprising the reference spatial resolution.

20. The method of claim 1 wherein applying the filter algorithm comprises:

applying a first Fourier Transform operation to a single line of the acquired image;

filtering a frequency space one-dimensional data of the acquired image; and performing a second Fourier Transform operation to obtain an image comprising the reference spatial resolution;

repeating the applying, filtering and performing steps on all lines that are parallel and perpendicular to the single line.

21. The method of claim 1 wherein applying the filter algorithm comprises filtering absorption data.

22. The method of claim 21 wherein filtering of the absorption data comprises filtering prior to reconstruction.

23. The method of claim 22 wherein reconstruction is a back projection.

24. The method of claim 1 wherein applying the filtering algorithm comprises applying a two-dimensional operator to the image.

25. The method of claim 1 wherein filtering comprises applying a one-dimensional operator to a line of the image;

repeating the applying step to all lines that are parallel to the line; and repeating the applying step to all lines that are perpendicular to the line.

26. A system for improving coronary and other vessel calcium scoring consistency, the system comprising:

an imaging unit that measures a spatial resolution of an image of a phantom; and a computer system coupled to the imaging unit, the computer system comprising:

a memory that stores a reference spatial resolution;

means for creating a resolution-adjusted image of an acquired image in which the spatial resolution of the acquired image is adjusted to match the reference spatial resolution, the adjustment being based on a comparison of the measured spatial resolution of the image of the phantom with the reference spatial resolution stored in the memory; and means for computing a coronary calcium score from a resolution-adjusted image generated by the means for creating.

27. The system of claim 26 wherein the phantom comprises a plurality of objects having known characteristics.

28. The system of claim 27 wherein the plurality of objects comprises aluminum wires having varied diameters which are between 0.1 and 3.0 times the spatial resolution of the imaging unit.

29. The system of claim 26 wherein the imaging unit is a CT scanner.

30. The system of claim 26 wherein the coronary calcium score is an Agatston Score.

31. The system of claim 26 wherein the coronary calcium score is a volume score.

32. The method of claim 26 where the coronary calcium score is an integral score.

33. A method of improving the consistency of coronary calcium scoring, the method comprising:

comparing a spatial resolution of the imaging scanner against a reference spatial resolution;

choosing a filter algorithm based on the comparison of the spatial resolution of the imaging scanner and the reference spatial resolution;

subsequent to choosing a filter algorithm, performing an imaging operation on the imaging scanner to obtain an image of a subject;

applying the filter algorithm to the obtained image to create a filtered image that has a spatial resolution that substantially matches the reference spatial resolution; and computing a coronary calcium score from the filtered image.

34. The method of claim 33 wherein the spatial resolution of the imaging scanner and reference spatial resolution are a full width half maximum.

35. The method of claim 33 where the coronary calcium score is an Agatston Score.

36. The method of claim 33 where the coronary calcium score is a volume score.

37. The method of claim 33 where the coronary calcium score is an integral score.

38. The method of claim 33 wherein the calcium scores from the filtered images are input into a database for comparison with scores from other images that comprise the reference spatial resolution.

39. The method of claim 33 wherein measuring is carried out periodically.

40. The method of claim 39 wherein periodically comprises once a day.

41. The method of claim 33 wherein the spatial resolution of the imaging scanner is based on a image of a phantom comprising a plurality of aluminum wires of different dimensions embedded in a low density matrix.

42. The method of claim 41 wherein the aluminum wires comprise a diameter that is between approximately 0.1 times the full width half maximum of the imaging device and 3.0 times the full width half maximum of the imaging device.

43. The method of claim 41 wherein measuring the spatial resolution of the phantom comprises measuring a peak absorption signal for each wire.

44. The method of claim 33 wherein comparing is carried out with software.

45. The method of claim 33 wherein the imaging device is a CT scanner.

46. The method of claim 45 wherein applying the filter algorithm comprises filtering data from detectors of the CT scanner before a reconstruction yields the image.

47. The method of claim 46 wherein applying the filter algorithm comprises multiplying a signal distribution of the images along the detectors by a set of weights that yield the reference spatial resolution.

48. The method of claim 46 where the reconstruction is a back projection.

49. The method of claim 33 wherein the filter algorithm performs at least one of smoothing and sharpening of the acquired images.

50. The method of claim 33 wherein applying the filter algorithm comprises convolving the image with one of a Gaussian filter, Fourier filter, or a cubic filter so that the spatial resolution of the images are adjusted to the reference spatial resolution.

51. The method of claim 33 wherein applying the filter algorithm comprises:

applying a first Fourier Transform to the acquired image;

filtering a frequency space two-dimensional data of the acquired image; and performing a second Fourier Transform to obtain an image comprising the reference spatial resolution.

52. The method of claim 33 wherein applying the filter algorithm comprises:
applying a first Fourier Transform to a single line of the acquired image;
filtering a frequency space one-dimensional data of the acquired image; and
performing a second Fourier Transform to obtain an image comprising the reference spatial resolution;
repeating the applying, filtering, and performing steps on all lines that are parallel and perpendicular to the single line.

53. The method of claim 33 wherein applying the filter algorithm comprises filtering absorption data.

54. The method of claim 53 wherein filtering of the absorption data comprises filtering prior to reconstruction.

55. The method of claim 54 wherein reconstruction is a back projection.

56. The method of claim 33 wherein applying the filtering algorithm comprises applying a two-dimensional operator to the image.

57. The method of claim 33 wherein filtering comprises applying a one-dimensional operator to a line of the image;
repeating the applying step to all lines that are parallel to the line; and
repeating the applying step to all lines that are perpendicular to the line.

58. A method of improving a comparison of calcium scores, the method comprising:
providing an algorithm;
obtaining at least one image with an imaging device;
applying the algorithm to the obtained image(s) to adjust a spatial resolution of the obtained image(s) to create resolution-adjusted image(s) that have a spatial resolution that substantially matches a reference spatial resolution; and
computing a coronary calcium score by performing a scoring operation on the resolution-adjusted image(s).

59. The method of claim 58 wherein providing comprises periodically measuring the spatial resolution of the imaging device and adjusting the algorithm based on the measuring of the spatial resolution of the imaging device.

60. The method of claim 59 wherein periodically monitoring occurs once a day.

61. The method of claim 59 wherein periodically monitoring comprises:
imaging a phantom;
comparing the spatial resolution of the imaged phantom to a reference spatial resolution; and
generating the algorithm that adjusts the spatial resolution of the imaged phantom to substantially match the reference spatial resolution.

62. The method of claim 61 wherein the phantom comprises a plurality of wires that have a diameter that is between approximately 0.1 times as large as a full width half maximum of the imaging device and 3.0 times as large as the full width half maximum of the imaging device.

63. The method of claim 58 wherein applying the algorithm comprises at least one of smoothing and sharpening the obtained image.

64. The method of claim 58 wherein the coronary calcium score is an Agatston Score.

65. The method of claim 58 wherein the coronary calcium score is a volume score.

66. The method of claim 58 where the coronary calcium score is an integral score.

* * * * *